(12) United States Patent
Spiegel et al.

(10) Patent No.: US 10,231,692 B2
(45) Date of Patent: Mar. 19, 2019

(54) ABDOMINAL STATISTICS PHYSIOLOGICAL MONITORING SYSTEM AND METHODS

(71) Applicants: THE REGENTS OF THE UNIVERSITY OF CALIFORNIA, Oakland, CA (US); THE UNITED STATES OF AMERICA REPRESENTED BY THE DEPARTMENT OF VETERANS AFFAIRS, Washington, DC (US)

(72) Inventors: Brennan Spiegel, Los Angeles, CA (US); William Kaiser, Los Angeles, CA (US); Vincent Zegarski, Los Angeles, CA (US); Digvijay Singh, Los Angeles, CA (US)

(73) Assignees: THE REGENTS OF THE UNIVERSITY OF CALIFORNIA, Oakland, CA (US); THE UNITED STATES OF AMERICA REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 15/641,126

(22) Filed: Jul. 3, 2017

(65) Prior Publication Data
US 2017/0340306 A1 Nov. 30, 2017

Related U.S. Application Data

(63) Continuation of application No. PCT/US2016/012375, filed on Jan. 6, 2016.
(Continued)

(51) Int. Cl.
*A61B 7/04* (2006.01)
*A61B 5/00* (2006.01)
(Continued)

(52) U.S. Cl.
CPC ............... *A61B 7/04* (2013.01); *A61B 5/002* (2013.01); *A61B 5/0022* (2013.01);
(Continued)

(58) Field of Classification Search
CPC ......... A61B 7/04; A61B 5/002; A61B 5/0022; A61B 5/4255; A61B 5/6823; A61B 7/008
(Continued)

(56) References Cited

U.S. PATENT DOCUMENTS

| 7,520,861 B2 * | 4/2009 | Murphy | ............... A61B 5/061 600/529 |
| 9,474,482 B2 * | 10/2016 | Devanaboyina | ..... A61B 5/0024 |

(Continued)

FOREIGN PATENT DOCUMENTS

| WO | 2013170018 A1 | 11/2013 |
| WO | 2014039404 A1 | 3/2014 |

OTHER PUBLICATIONS

Korean Intellectual Property Office (KIPO), International Search Report and Written Opinion, dated Apr. 25, 2016, counterpart PCT international application No. PCT/US2016/012375, pp. 1-14, with claims searched, pp. 15-20.

(Continued)

*Primary Examiner* — Xu Mei
(74) *Attorney, Agent, or Firm* — O'Banion & Ritchey LLP; John P. O'Banion

(57) ABSTRACT

An abdominal statistics system including a low profile rapidly deployable sensor element having an acoustic sensor and vibration actuator that can be conveniently attached to the abdomen of a patient. The system acquires acoustic signals as gastrointestinal (GI) sounds, processes these signals, and provides actionable data to patients and their providers.

20 Claims, 14 Drawing Sheets

Related U.S. Application Data

(60) Provisional application No. 62/100,367, filed on Jan. 6, 2015.

(51) Int. Cl.
*A61B 7/00* (2006.01)
*G06F 17/18* (2006.01)
*G06F 19/00* (2018.01)
*G16H 40/67* (2018.01)

(52) U.S. Cl.
CPC ............ *A61B 5/4255* (2013.01); *A61B 7/008* (2013.01); *G06F 17/18* (2013.01); *G06F 19/00* (2013.01); *G16H 40/67* (2018.01); *A61B 5/6823* (2013.01)

(58) Field of Classification Search
USPC .................................. 381/67; 600/528, 586
See application file for complete search history.

(56) References Cited

U.S. PATENT DOCUMENTS

| | | | |
|---|---|---|---|
| 2002/0156398 A1* | 10/2002 | Mansy | A61B 7/008 600/586 |
| 2003/0153847 A1 | 8/2003 | Sandler | |
| 2009/0248114 A1 | 10/2009 | Ganion | |
| 2012/0172839 A1* | 7/2012 | Chappa | A61L 29/085 604/509 |
| 2014/0303520 A1 | 10/2014 | Telfort | |

OTHER PUBLICATIONS

European Patent Office (EPO), Communication (The extended European search report) dated Jun. 22, 2018, related European patent application No. EP16735370.5, pp. 1-9, claims searched, pp. 10-13.

* cited by examiner

ABDOMINAL STATISTICS PHYSIOLOGICAL MONITORING SYSTEM AND METHODS

CROSS-REFERENCE TO RELATED APPLICATIONS

This application is a 35 U.S.C. § 111(a) continuation of PCT international application number PCT/US2016/012375 filed on Jan. 6, 2016, incorporated herein by reference in its entirety, which claims priority to, and the benefit of, U.S. provisional patent application Ser. No. 62/100,367 filed on Jan. 6, 2015, incorporated herein by reference in its entirety. Priority is claimed to each of the foregoing applications.

STATEMENT REGARDING FEDERALLY SPONSORED RESEARCH OR DEVELOPMENT

This work was supported by the U.S. Department of Veterans Affairs, and the Federal Government has certain rights in the invention.

The above-referenced PCT international application was published as PCT International Publication No. WO 2016/112127 on Jul. 14, 2016, which publication is incorporated herein by reference in its entirety.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to generally to abdominal monitoring, and more particularly to monitoring for abdominal dysfunctions.

2. Background Discussion

There are currently no commercially-available systems that provide continuous, wireless, abdominal physiologic monitoring across the spectrum of abdominal dysfunctions that we describe herein. The "state of the art" includes conducting intermittent abdominal examinations with a stethoscope and manual palpation.

Abdominal dysfunctions may include a broad spectrum of indications. For example, most every patient develops temporary bowel paralysis following thoracic, abdominal, or pelvic surgeries. Clinicians monitor stool output and bowel sounds to determine when it is safe to begin re-feeding and to plan hospital discharge. Patients with prolonged bowel paralysis can require additional hospital days and excessive stays.

Patients with an acute abdomen are highly prevalent in medical, surgical, pediatric, and obstetrical inpatient wards, and include those with acute cholecystitis, pancreatitis, appendicitis, colitis, diverticulitis, bowel ulcerations or perforations, and bowel obstructions, among many other conditions. These high acuity patients often have a dynamic and unpredictable clinical course and require frequent monitoring. Although acutely ill patients often have continuous cardiovascular and pulmonary monitoring, they do not have continuous abdominal monitoring. Yet, changes in the abdomen almost always precede changes in cardiovascular and pulmonary function in patients with acute abdominal disorders.

Cirrhosis is highly prevalent, and ascites (abdominal fluid accumulation) is a common complication of portal hypertension in chronic liver disease. Ascites also occurs in a range of other conditions, including abdominal infections and cancer. Patients with ascites can be difficult to manage and require frequent changes in their diuretic (water pill) dosing, amount of sodium restriction, and dietary composition.

Narcotics are commonly used in healthcare. Patients with chronic pain, in particular, are highly prevalent in both the inpatient and outpatient settings. A major complication of narcotics is bowel paralysis, leading to ileus or even Ogilve's syndrome (colonic inertia). For inpatients, bowel paralysis can lead to prolonged stays and increased healthcare costs. For outpatients, bowel paralysis can impact compliance with otherwise effective therapies. For both groups, narcotics cause disruptive consequences of GI distress, and ultimately diminished health related quality of life.

Inflammatory bowel diseases, including Crohn's disease and ulcerative colitis, are common conditions in GI practice. Patients with Crohn's Disease, in particular, often suffer from intermittent bowel obstructions related to intestinal strictures. Managing these patients can be challenging and not well suited to the usual approach of intermittent appointments and clinic visits. The disease can be dynamic, and bowel obstructions may occur between clinic visits, leading patients to the emergency department for urgent management.

Chronic or recurrent abdominal pain is highly common both in GI and general medicine clinics. Although various imaging tests are commonly used to evaluate the source of pain (e.g. computerized tomography, magnetic resonance, etc.), there are very few functional tests of abdominal physiology. Most tests of abdominal function (e.g. esophageal or gastric motility, "Smartpill," Sitzmark studies, etc.) are highly specialized, invasive, expensive, and limited to specialized motility centers. Moreover, these tests only measure health over a short period of time, typically much less than a day.

Bloating is among the most common symptom experienced by people in the community, and certainly in GI practices. Despite being common, little is known about its pathophysiology, and even less is available to manage the condition. However, there are ways to manage bloating if they are aligned with the underlying physiology. For example, most patients with bloating have a learned reflex where the anterior abdominal wall is actively relaxed, forcing the abdomen to literally "pooch out" with lowering of the diaphragm. This form of "functional bloating" is different from increased intra-abdominal gas, where the abdominal wall does not relax.

Nausea and vomiting are highly disruptive symptoms. Although the underlying etiology is often apparent from diagnostic testing, many patients continue to have unexplained nausea and vomiting despite costly and extensive work-ups.

Patients with diarrhea and incontinence may suffer from many different conditions with different physiologic mechanisms. Patients with fecal incontinence, in particular, can be difficult to diagnose and treat.

Constipation is also extremely common. Gastroenterologists divide constipation into 3 major forms: (1) slow transit, (2) normal transit, and (3) pelvic dyssynergia. There are invasive tests to help separate these forms of constipation, but they are expensive, only available in specialized centers, and provide only short-term data.

IBS affects ~10% of the world's population, and is among the most common conditions experienced by man. Marked by abdominal pain and defecatory symptoms, IBS is not only common, but also a significant impact on the quality of life. Current theories of IBS suggest an abnormality in the "brain-gut axis," with both central and peripheral disease mechanisms. The "stress" theory of IBS suggests that GI symptoms arise from visceral anxiety driven through a combination of stress hormones and their function on GI physiology. Peripheral theories include abnormal motility, inflammatory changes in the intestines, and bacteria, among others. Patients with IBS have recurrent symptoms that can be dynamic and unpredictable. It is difficult to monitor the condition correctly, yet diagnostic and therapeutic decision making depends on valid and reliable patient reporting of their illness.

Regardless of the underlying condition, GI patients often need to keep an accurate bowel diary to help monitor disease, treatments, and collect diagnostic information for their providers. But bowel diaries are frequently inaccurate and patients often forget to complete the diary or even fail to begin.

In the setting of cardiovascular diseases, such as hypertension, smoking, and hyperlipidemia, the abdominal aorta can develop atherosclerotic changes. Over time, this leads to aneurysm formation, itself potentially dangerous; aortic hemorrhage can be rapidly fatal. Patients with known "triple As" (AAA) are typically monitored with serial ultrasounds. But AAAs can change rapidly between scheduled ultrasounds. Continuous acoustic monitoring can listen to the continuous "hum" of an AAA, and track changes in the acoustic signature. Marked changes might indicate expansion or other morphological changes of the lesion, and therefore prompt more timely investigation before a potential catastrophe.

BRIEF SUMMARY

The abdominal statistics (Abstats) system of the present description comprises a noninvasive, convenient and low cost system exploiting disposable components for rapid assessment of important digestive disorders. The system serves an urgent and unmet need for serving patients and any individual with digestive monitoring diagnostic capability. It has the potential to penetrate multiple markets quickly, provide irreplaceable clinical data, offer a novel way for patients and providers to track disease between scheduled visits, offer the general public a way to quantify their own physiology, and ultimately reduce the cost of healthcare delivery. In addition, the system offers many important applications for veterinary medicine, described later in this document.

The abdominal statistics system of the present description includes multiple product configurations including a low profile rapidly deployable sensor element that can be conveniently attached to the abdomen of a patient by either a belt or adhesive attachment method. The system acquires acoustic signals as gastrointestinal (GI) sounds, processes these signals, and provides actionable data to patients and their providers.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Figure 1:
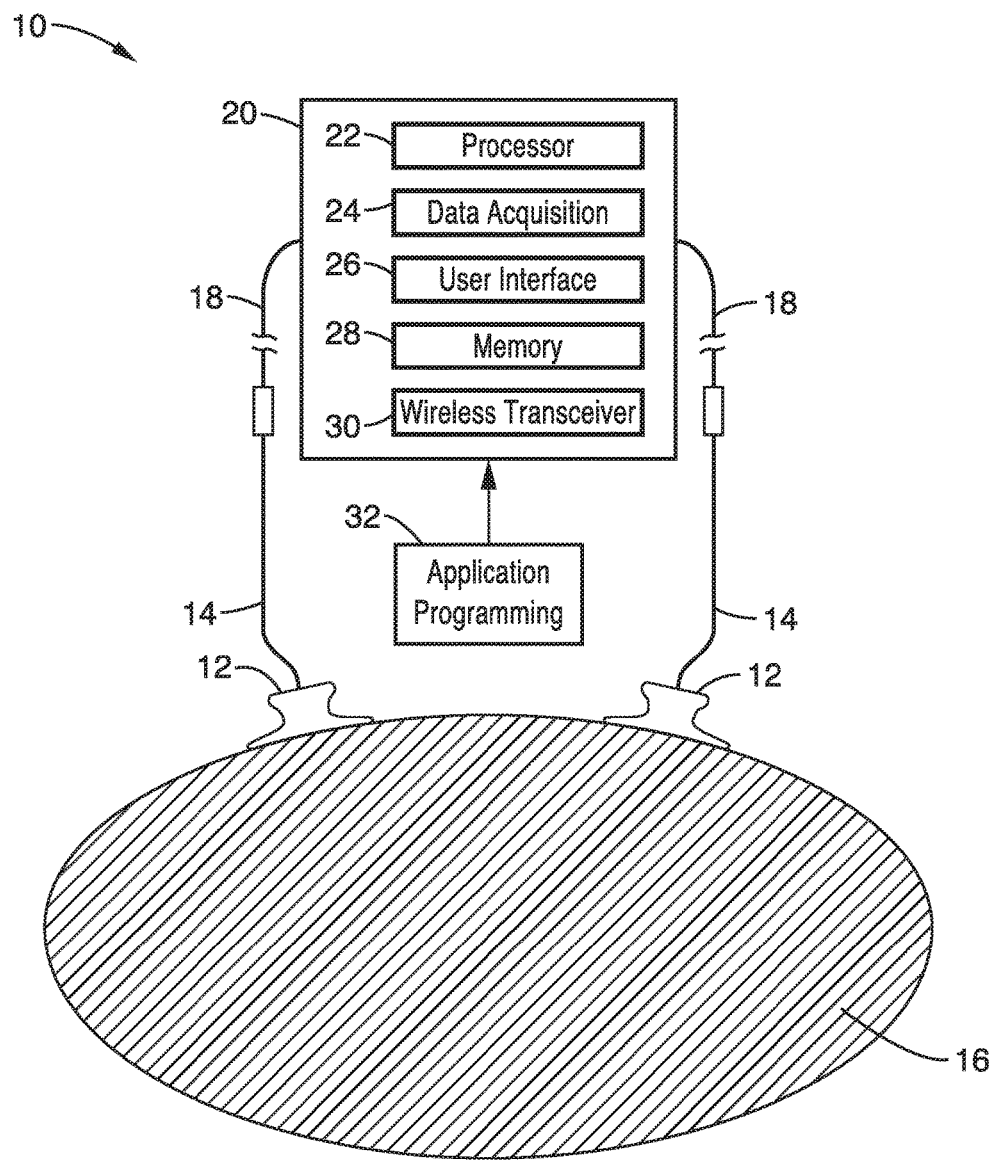
FIG. 1 illustrates an abdominal statistics system with a disposable sensor applied to the abdominal wall epidermis of a patient according to an embodiment of the technology of this disclosure.

Referring to FIG. 1, one embodiment of the multi-sensor wireless abdominal statistics monitoring system 10 comprises a plurality of low profile highly focused acoustic sensors 12 that are applied to the anterior wall of abdomen 16, e.g. to perform acoustic monitoring to measure the sounds of motility emanating from the gastrointestinal tract and to measure heart rate by monitoring abdominal arterial pulse.

FIG. 1 illustrates a high level schematic diagram of a system 10 with a two-sensor linear array of digital stethoscope transducers 12 according to a preferred embodiment of the invention. The sensors 12 are shown adhered to the abdomen 16 in FIG. 1, but may also be supported by an elastic waist belt (not shown) that is configured to circumscribe the patient's abdomen 16.

It will be appreciated that other sensor configurations are possible as needed for multiple-sensor scenarios. In the case of the 2-sensor system shown in FIG. 1, with one sensor 12 may be positioned such that it lines up adjacent to the right lower quadrant of the abdomen 16 over the region of the ileocecal valve (not shown), and the other sensor 12 lining up adjacent the left lower quadrant of the abdomen 16 over the sigmoid colon (not shown).

These acoustic sensors 12 are configured to continuously and non-invasively monitor and capture a range of audio signals which represent gastrointestinal and abdominal wall functions. The captured data is recorded by the system 10 in a synchronized manner from all onboard sensors 12. The data acquired by the sensors 12 are fed to a gateway controller 20, which houses signal processing and data acquisition circuitry. A data acquisition unit 24 and processor 22 acquire the raw data from the sensors 12. The unit may have a user interface 26 for user manipulation of the device via a display (not shown), and memory 28 for storing the acquired data and/or programming 32 associated with data acquisition/signal processing, as described in further detail below. A wireless transceiver 30 may also be included for transferring the acquired sensor data and/or configuration data to a central repository or database (not shown).

Figure 2:
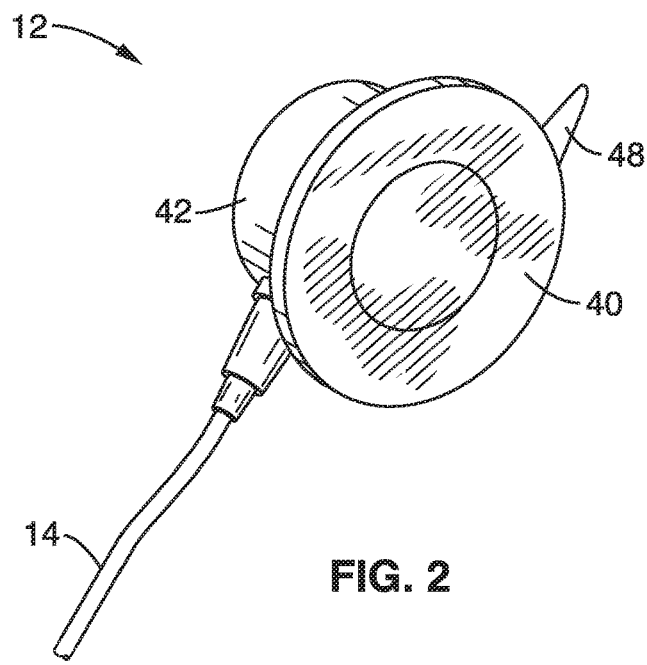
FIG. 2 shows a perspective view of the disposable sensor of FIG. 1.

FIG. 2 illustrates an exemplary abdominal statistics disposable sensor 12, showing the underside of the sensor prior to adhesion to an area of the patient (e.g., abdominal area) for which digestive statistics are to be collected. Each sensor generally comprising a housing 42 for securely holding various sensing components, and an annular flange 40 for coupling to the patient's skin via adhesive attachment or bandage 48.

The abdominal statistics system 10 acquires acoustic signals as gastrointestinal (GI) sounds using the sensors 12 shown in FIG. 2, and described in detail in the following sections. The abdominal statistics sensors 12 are preferably supported by the abdominal statistics gateway or controller 20, which may comprise a compact electronic device with integrated sensor interfaces, embedded computing system, and display.

The abdominal statistics gateway controller 20 may include an input/output device, exemplified as a touchscreen display (e.g., LCD display 90 shown in FIG. 5), along with various electrical connections for coupling to various devices such as the abdominal statistics sensors 12.

The abdominal statistics system 10 is configured to enable rapid deployment of abdominal statistics sensors on patients in a way that enables disposable patient-contacting devices that eliminate the need for cleaning and disinfection. These features preferably include one or more of the following: 1) abdominal statistics disposable sensor systems with wound care bandage materials to enable biocompatibility and long term wear by the patient, 2) compatibility with multiple wound care adhesive bandages, 3) compatibility with an adhesive bandage (e.g. Tegaderm, 3M) to be readily incorporated with the sensor housing 42 for attaching for adhering to the skin surface of abdomen 16, and 4) disposable cable systems providing assurance of avoidance of contamination.

Figure 3:
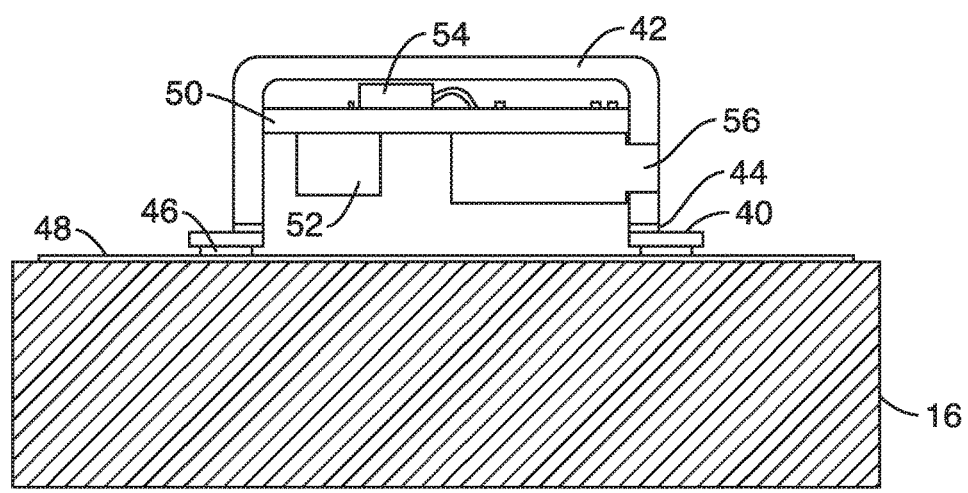
FIG. 3 shows a side view of the sensor of FIG. 1 coupled with the a bandage for adhering to the skin surface.

In the side view of FIG. 3, a sensor 12 is shown with housing 42 bonded (e.g., via adhesive 44) to a mounting flange 40, under which is an adhesive mounting ring 46 shown coupled to a bandage 48 (e.g. Tegaderm bandage). It is appreciated that other bandage types and brands may be utilized with the abdominal statistics system 10 for attachment to patient abdominal tissue 16. Held within the sensor housing 42 is a printed circuit board 50 (of any desired material in the art), upon which are attached a sensor electrical connection 56, a sensor microphone 52, and a sensor vibration actuator 54. The sensor connection 56 is shown in FIG. 3 by way of example as an audio jack, although the device may alternatively utilize other connector forms available in the art, or provide a wire pigtail extending from the housing 42. In addition, certain embodiments of the sensor device 12 may be configured with passive and/or active electronic components for conditioning microphone inputs and vibration actuator outputs.

Sensors 12 are preferably coupled to gateway/controller 20 via an attachment cable 14 that may include or comprise a disposable sensor interconnection cable (see cable 18a/18b shown in FIG. 4) for data acquisition, data processing, and data display. As illustrated in FIG. 2, a simple stereo audio jack may be employed having a shield wire and two wires to carry an audio signal from the microphone 52. It will be appreciated that these disposable cables 14 may be configured with various forms of mating connectors and wiring, insofar as they mate with the gateway controller 20, without departing from the teachings of the present disclosure.

The abdominal statistics sensor module 12, including sensing and acoustic sources, ideally provides assurance of usage to enable advanced system reliability that is critical for a wide range of applications. "Assurance of usage" is the process by which the abdominal statistics system 10 may automatically verify that both sensors 12 of a dual sensor set are coupled properly to the abdomen 16 in order to properly receive abdominal vibration. In one embodiment, assurance of usage is enabled by the deployment of dual sensors 12 that each contain active acoustic sources 54 (e.g. vibration actuator or other motor system) in addition to sensor elements.

The vibration actuator 54 operation may be scheduled to occur at intervals during system operation. Intervals may vary from seconds to many minutes determined by desired usage assurance requirements.

In one exemplary configuration, the vibration actuator 54 is preferably operated for intervals of 0.1 to 1 second, although other intervals may be selected.

Figure 10:
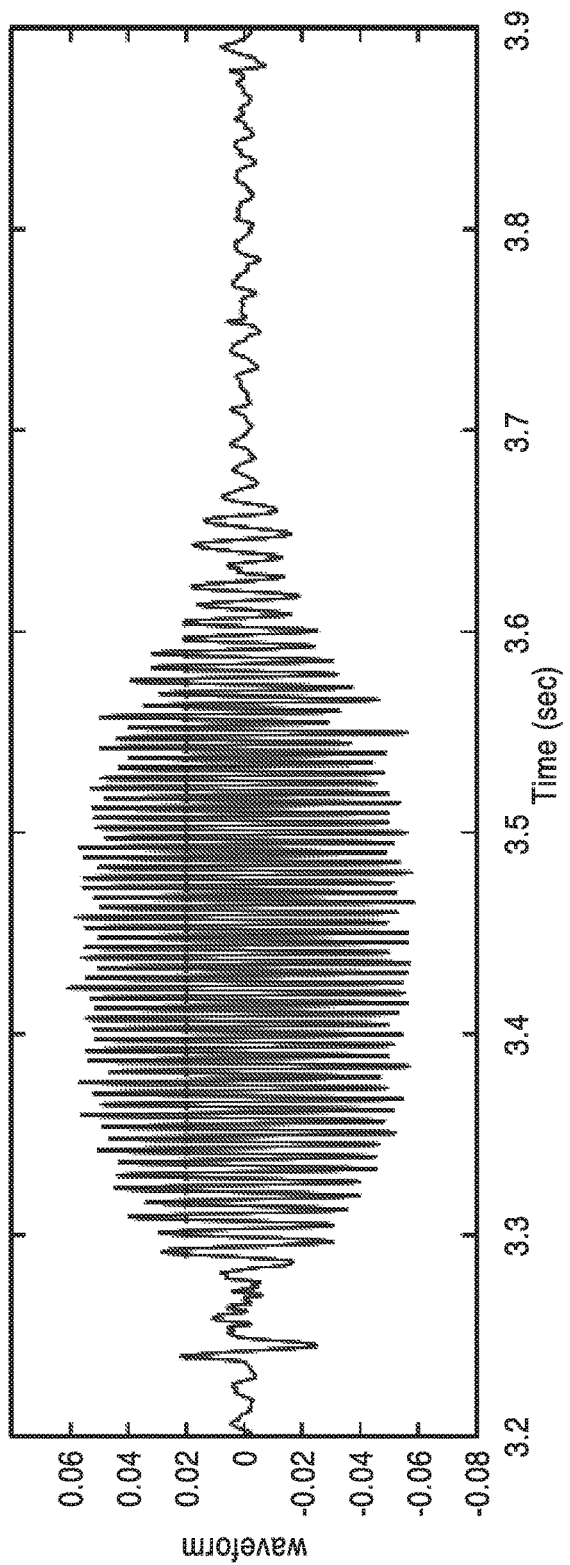
FIG. 10 shows a graph that illustrates a narrow band waveform.

The vibration actuator 54 induces vibration into the sensor housing 42 that is then coupled to the patient abdomen 16 via flange 40. The vibration signal propagates between sensors from the emitting sensor to the receiving sensor and appears as a narrow band waveform as shown in FIG. 10.

Sensors 12 may also be alternately selected for emission and reception to ensure that usage assurance is enabled for both sensors. The vibration signal, emitted from the vibration actuator 54 within a first sensor 12 of a pair, is received by the microphone 52 of the second sensor 12 of a pair. If more than two sensors are applied, then the signal may be received by multiple sensors.

The sensor input signal is preferably filtered in the frequency domain to select the narrow band of frequencies associated with the frequency of the vibration signal, while its expected arrival time is also preferably factored in. Features in the received waveform that satisfy frequency domain and amplitude are detected as indicated by the line of indicating points at the 0.02 amplitude level in FIG. 10.

In this example, the waveform has been confirmed as being due to the vibration signal from a remote sensor, and thus verifies usage.

Figure 4A:
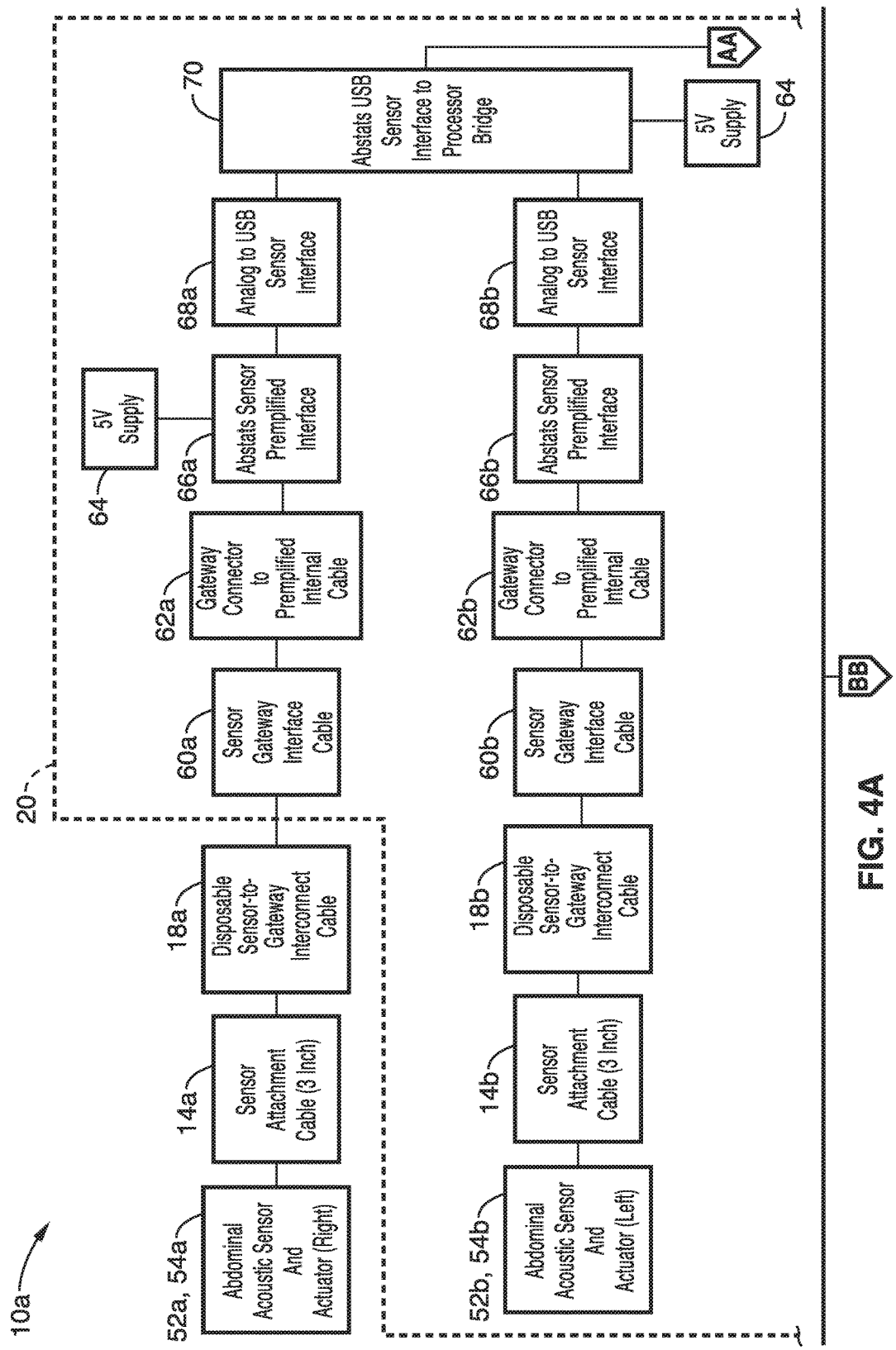
FIG. 4A and FIG. 4B show a schematic diagram of an abdominal statistics system architecture that includes sensor systems and a data acquisition, data processing, and data transmission gateway according to the technology of this disclosure.
Figure 4B:
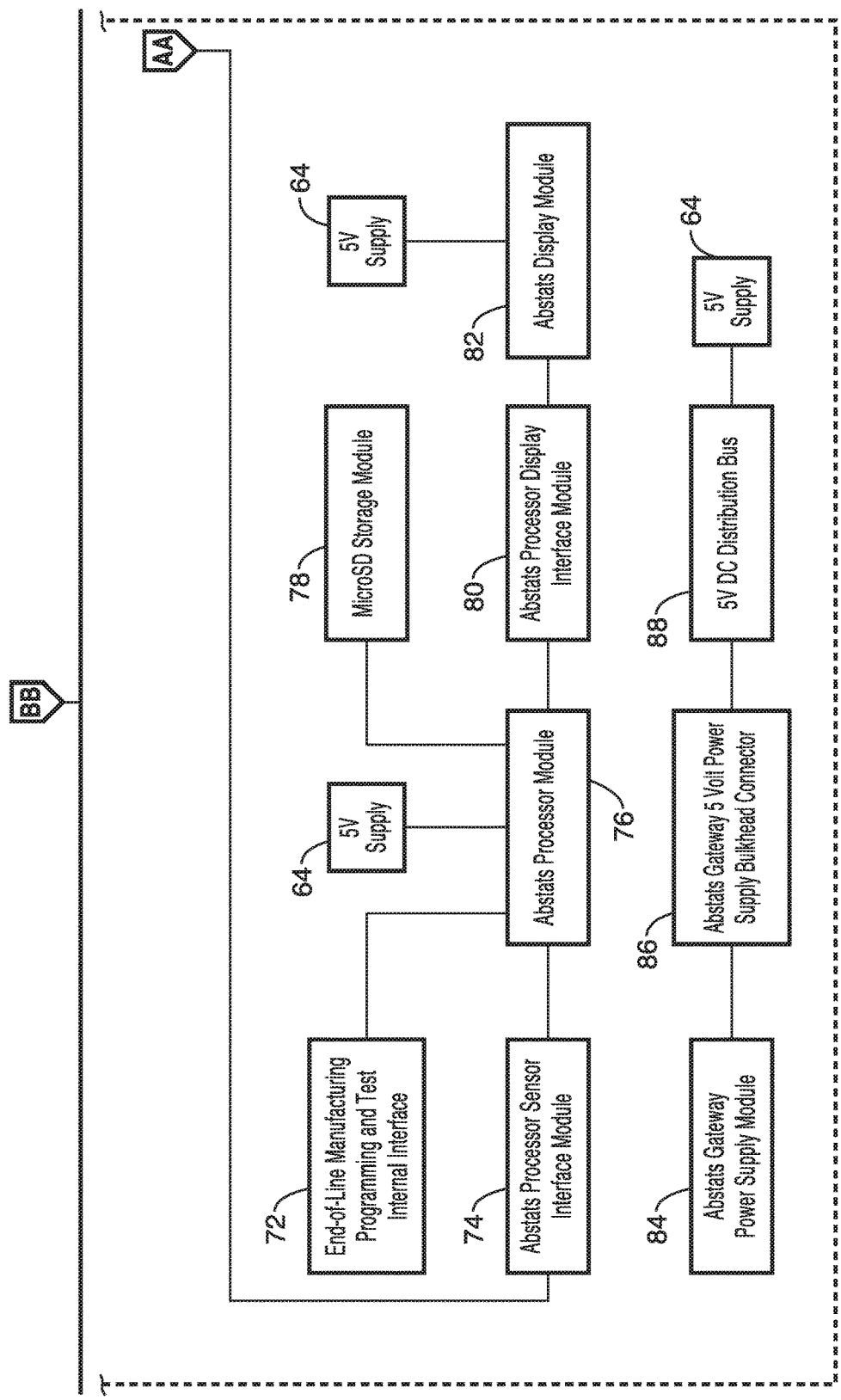

Referring to the block system diagram of FIG. 4A and FIG. 4B, system 10a may include an abdominal statistics sensor 12 and gateway controller 20 architecture for sensor systems and a data acquisition, data processing, and data transmission gateway. The block diagram of FIG. 4A and FIG. 4B is shown for an exemplary system configuration comprising two sensors 12 left (a) and right (b), and corresponding components directed to each sensor (e.g. sensor 12a for left sensor and 12b or right sensor). It is appreciated, however, that the system 10 may be configured for any number of sensors.

Abdominal acoustic sensors and actuators 52a/54a and 52b/54b (for left and right sensors, respectively) are coupled to attachment cables 14a/14b and disposable sensor to gateway connections 18a/18b, and sensor to gateway interface connectors 60a/60b to a gateway connector to preamplifier cable 62a/62b to preamplifier sections/interface 66a/66b (shown being supplied by power 64 (e.g., 5V). Output from the preamplifiers 66a/66b is coupled to an analog to digital sensor interface 68a/68b, e.g. for conversion to digital signals, and more particularly to conversion to digital signals over a universal serial bus (USB). The digital interface is seen coupled to a processor bridge 70, which is also shown supplied with operating power 64 (e.g., 5V).

The outputs from the processor bridge 70 are then received by the abdominal statistics processor sensor interface module that outputs to the abdominal statistics processor module 74, which is shown receiving operating power (e.g., 5V), and an end-of-line manufacturing programming and test internal interface 72. A programming and/or data storage module 78 is also shown coupled to the processor module 76, shown by way of example as a MicroSD storage module, although other forms of data store may be utilized without limitation. Output from the processor module 76 is received by an abdominal statistics processor display interface 80, which is coupled to the abdominal statistics display module 83 that also receives a source of power 64 (e.g., 5V).

The bottom row of components in FIG. 4B depicts different power supplies utilized in the example embodiment, such as a 5V supply 64 on the right to a DC distribution bus 88, then to a bulkhead connector 86, and finally to the gateway power supply module 86. It will be appreciated that power may be supplied to different blocks than shown and carried where needed. In addition, it should be appreciated that in certain applications (i.e., portable), the power may be supplied from one or more power storage units (e.g., batteries).

Figure 5A:
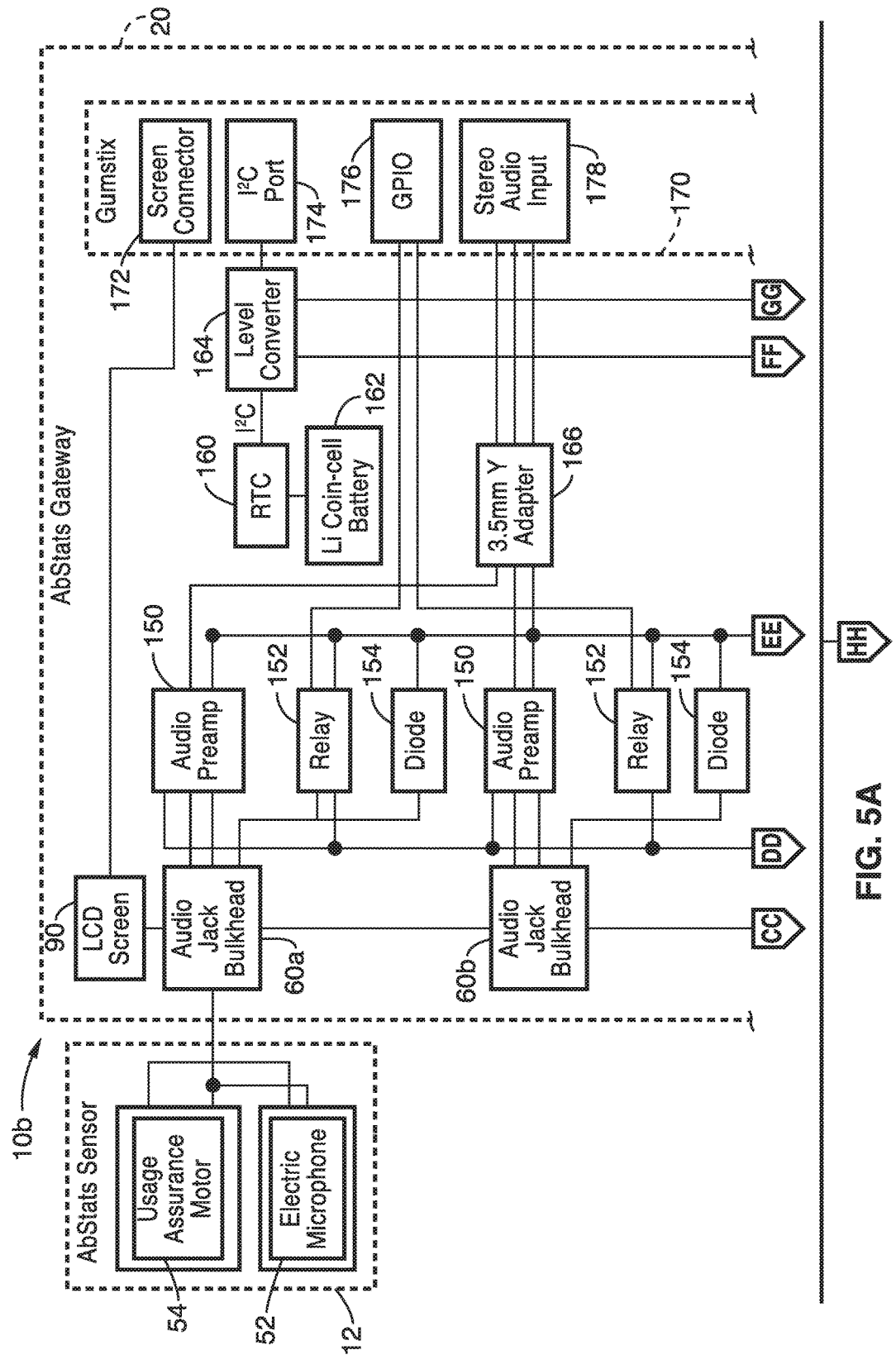
FIG. 5A and FIG. 5B shows a block diagram of an embodiment of the abdominal statistics system showing an abdominal statistics sensor, and a power supply coupled to an abdominal statistics gateway.
Figure 5B:
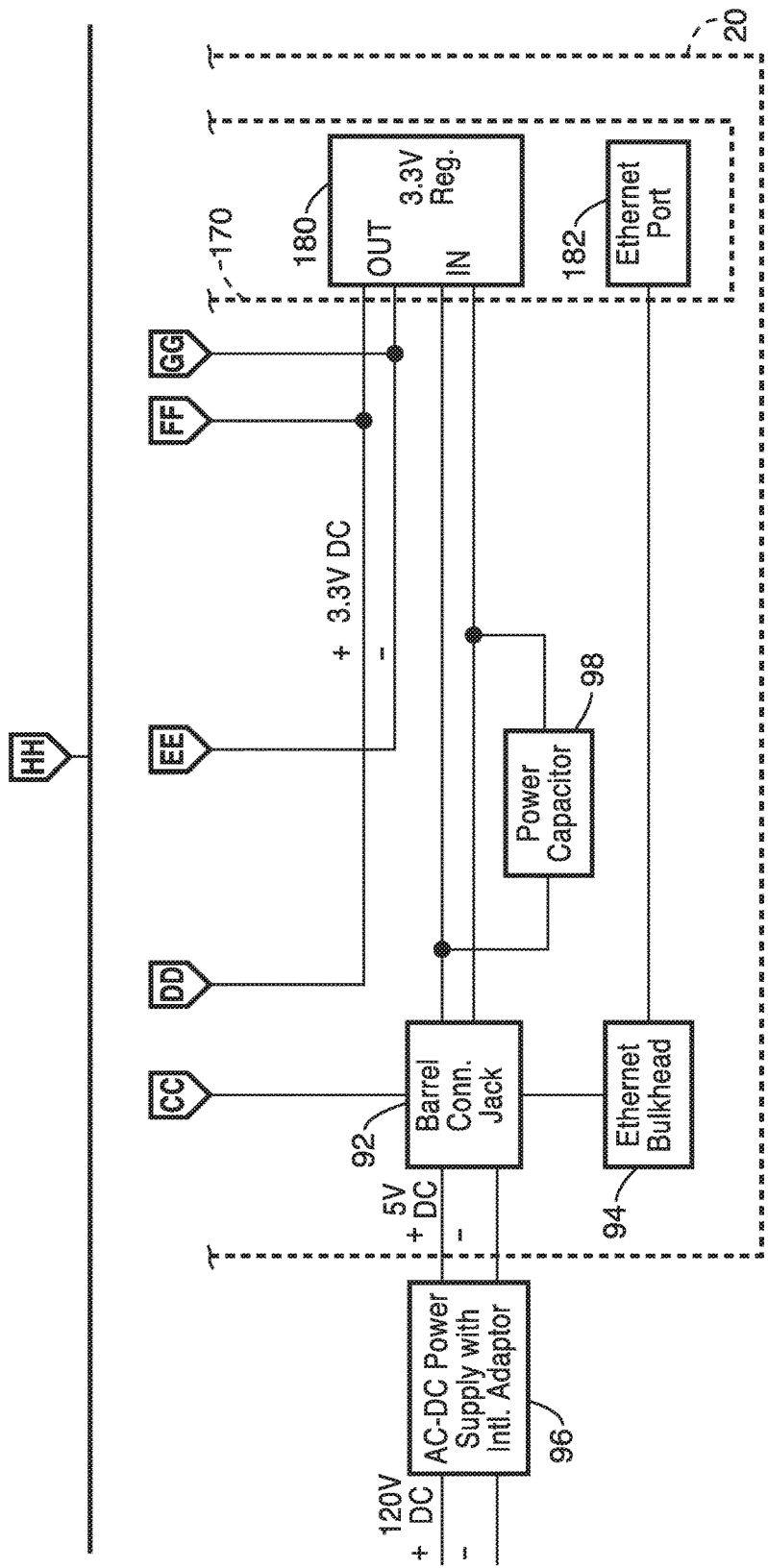

FIG. 5A and FIG. 5B show a block wiring diagram of an exemplary abdominal statistics system 10b, showing an abdominal statistics sensor 12, and a power supply 96 coupled to an abdominal statistics gateway controller 20. The abdominal statistics sensor 12 is comprises an actuator/usage assurance motor 54, and a microphone 52 with output connecting to an audio jack at the bulkhead 60a of the abdominal statistics gateway controller 20. The other connections to the abdominal statistics gateway controller 20 are depicted as an LCD screen 90, a second audio jack bulkhead 60b open to receive a second sensor 12, a barrel connection jack 92 to power supply 96, and an Ethernet connection 94. Connected to the audio jacks 60a/60b are audio preamps 150 for conditioning the microphone input, and relays 152 and diodes 154 for driving the assurance motor 54. A power capacitor 98 is coupled to the power input from the power supply 96. A real-time clock 160 with a backup power of a Li coin cell battery 162 is shown included with a level converter 164 at its connection with a microcontroller board 170 (e.g. Gumstix microcontroller or the like). The microcontroller board 170 is coupled to a screen connector 172 to the LCD screen 90, an I$^2$C port 174, a general purpose I/O port (GPIO) 176, a stereo audio input 178 (coupled to Y adapter 166), a voltage regulator 180 and an Ethernet port 182. The components detailed in FIG. 5 are detailed by way of example and not by way of limitation, as one of ordinary skill in the art will recognize that a wide range of circuitry could be substituted while providing the same general structure and functions of the present disclosure.

Figure 6:
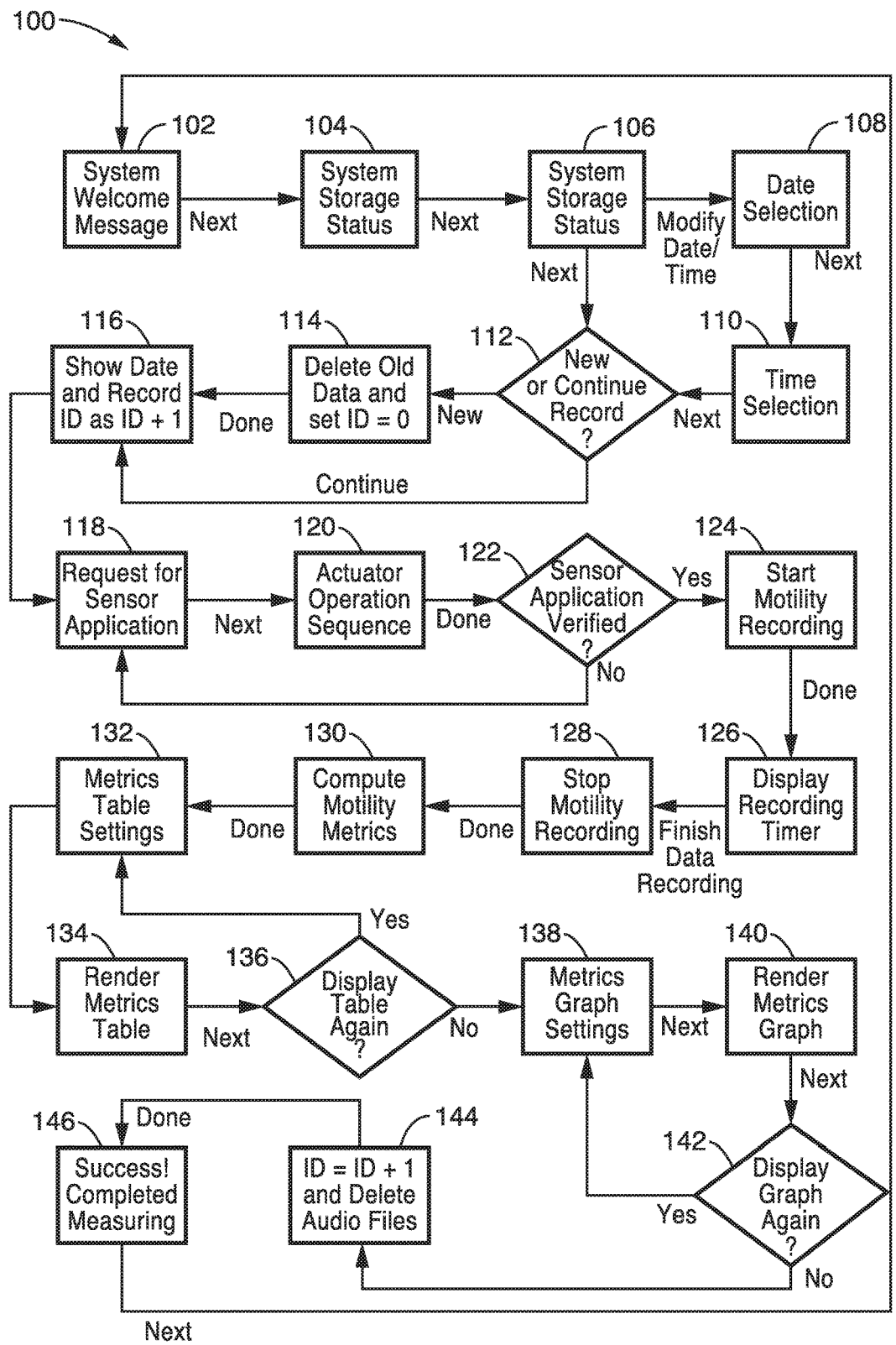
FIG. 6 shows a flow diagram of an exemplary abdominal statistics state process in accordance with the present description.
Figure 7:
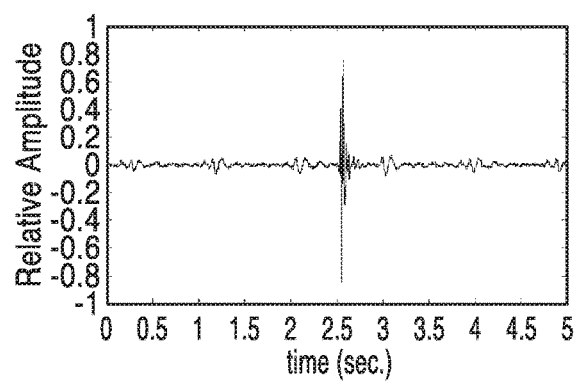
FIG. 7 and FIG. 8 illustrate plots of typical abdominal statistics acoustic signals corresponding to digestive motility events at 5 second (FIG. 7) and 800 msec (FIG. 8) intervals.
Figure 8:
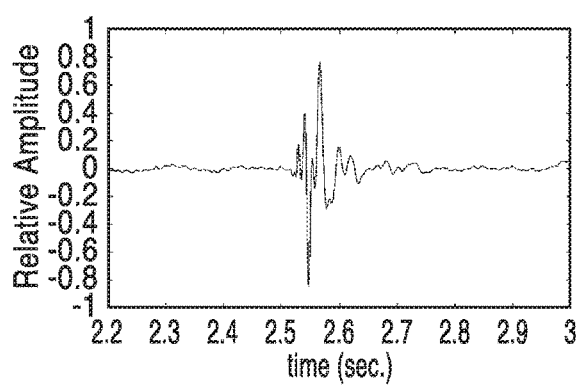
Figure 9:
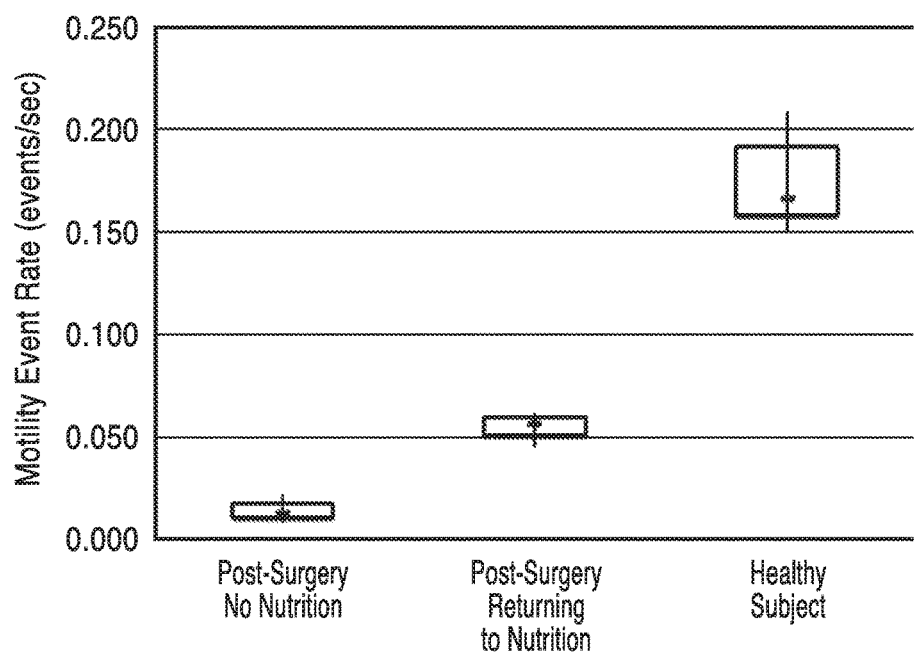
FIG. 9 is a graph that illustrates abdominal statistics trial results as a function of motility event rate.

FIG. 6 shows a flow diagram of an exemplary operating routine 100, which may be implemented as part of application software 32 of FIG. 1. The operating sequence commences in the upper left with a welcome message at block 102, then a determination (and optional display) of system storage status is made at block 104, along with collection (and optional display) of system date and time at block 106, which may be modified using the date selected first at block 108, then time at block 110.

Moving to the left in this second row, a decision is made at block 112 to make a new record or continue a previous recording. If it is a new record, then the old record is deleted and initialization is performed (e.g., ID=0) at block 114. For new and existing recording, the date and record ID is incremented and displayed at block 116.

Continuing at block 118 in the third row, a request is made (e.g., displayed and optionally annunciated) for the sensor to be applied to the patient. Sensor application is tested at block 120 by activating the actuator 54 and sensing an acoustic response via microphone 52. If the acoustic signature of the vibrations are not registered (e.g. at verification block 122), it is assumed the sensors have not both been applied, and execution returns to block 118. Otherwise, motility recording commences at block 124, with the recording timer being displayed at block 126. At this point the device is in its capture mode and collecting data for any selected or desired period of time. As data recording is finished, the recording is stopped at block 128.

Processing of the data is performed by computing motility metrics at block 130 and metrics table settings at block 132, after which the metrics table is rendered at step 134. The table may be displayed again at block 136, going back to the metrics table settings 132. Otherwise, metrics graph settings are selected at block 138 and a metrics graph is rendered at block 140. The graph may then be displayed again at block 142 going back to metrics graphs settings. Otherwise, the ID is incremented and audio files deleted at block 144, whereby the collecting of statistics has been a success and the measurements completed at block 146.

It should be appreciated that the flow of functions performed by the abdominal statistics system 10, as embodied in the method 100 of FIG. 6, may be significantly varied without departing from these teachings, while many of these functions may be performed simultaneously, or in a different order. In particular, it should be appreciated that in at least one embodiment various metrics can be processed and even displayed while the data is collected, instead of waiting until after data collection is finished.

The abdominal statistics application software 32 preferably includes acoustic analog signal processing, digital signal processing, computation, scheduling, and data display systems along with user interactive systems including a touch screen display.

The abdominal statistics gateway 20 may also include network access (via wireless interface 30 shown FIG. 1 or Ethernet port 182 shown in FIG. 5B), including wireless access to both local area as well as cellular wide area network access. Network access may also include connectivity to smartphone systems, as well as to enable remote access to centralized data systems via smartphone gateway architectures. The network access may also include connectivity to fixed based gateway systems as well as to enable remote access to centralized data systems. Abdominal statistics networking enables access to remote abdominal statistics software services for data storage, data distribution, and computation.

Signal processing and signal classification by the abdominal statistics system 10, and in particular application software 32, may be configured to apply the transmission and reception of probe signals produced by integrated acoustic emitter sources to provide assurance of usage, including the following characteristics and benefits:
 (a) Programs that sequence the transmission and reception of probe signals produced by integrated acoustic emitter sources.
 (b) Signal processing and signal classification routines that optimize data acquisition time by balancing time directed to usage assurance and time directed to motility signal acquisition.

In one configurations, abdominal statistics signal processing application programming 32 may apply the transmission and reception of probe signals produced by integrated acoustic emitter sources to provide calibration associated with unknown sensor coupling and subject tissue and organ acoustic signal transmission properties. For example, the software may be configured for measurement of amplitude and computation of path loss for acoustic transmission that may be applied to corrections for path loss associated with abdominal internal physiological signals.

Figure 11:
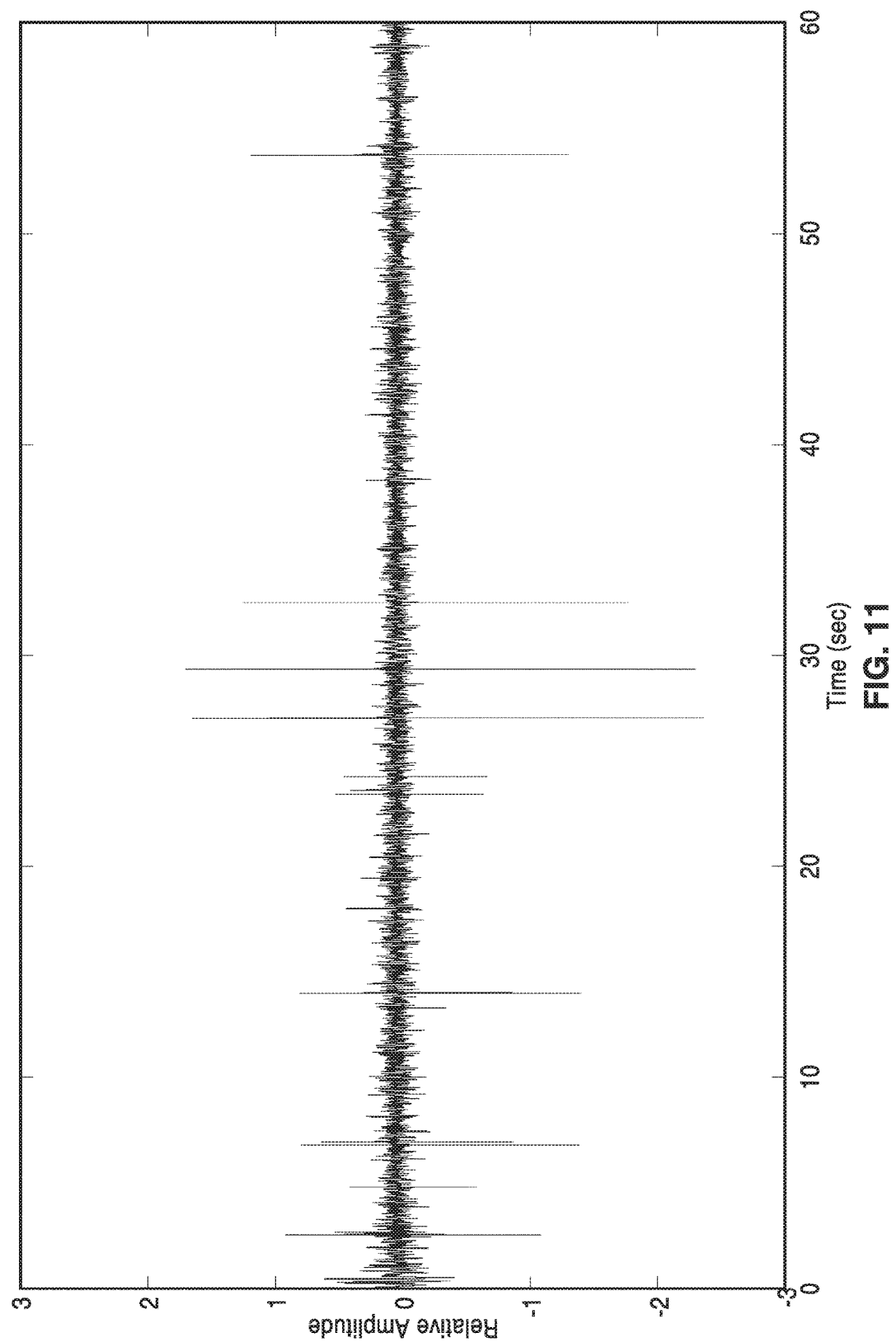
FIG. 11 through FIG. 13 show plots of time series profiles of a motility waveform at selected time segments.
Figure 12:
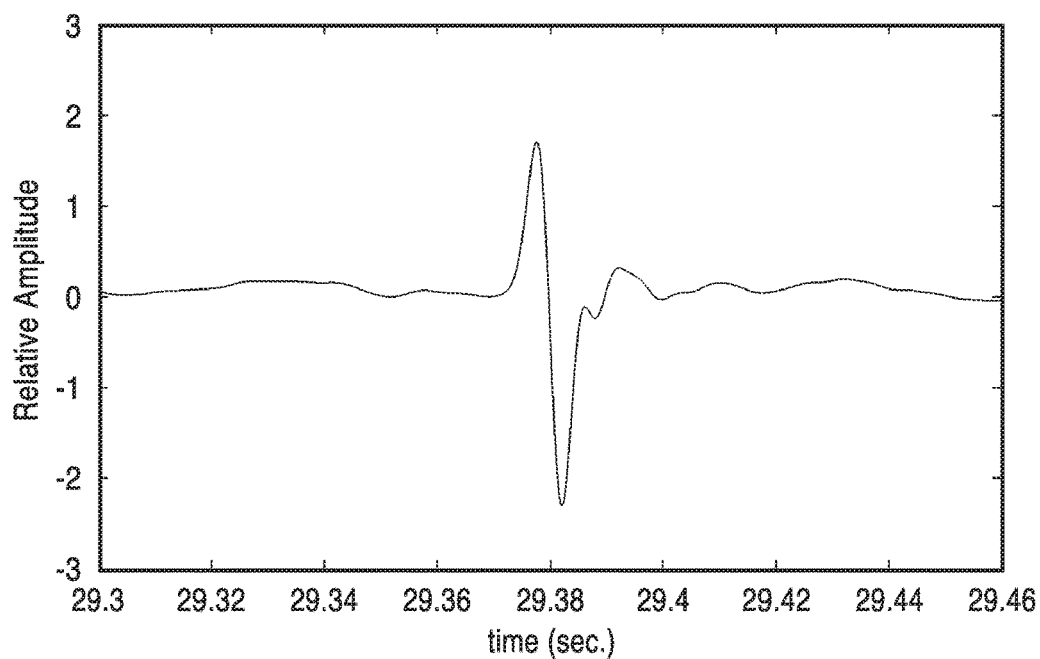
Figure 13:
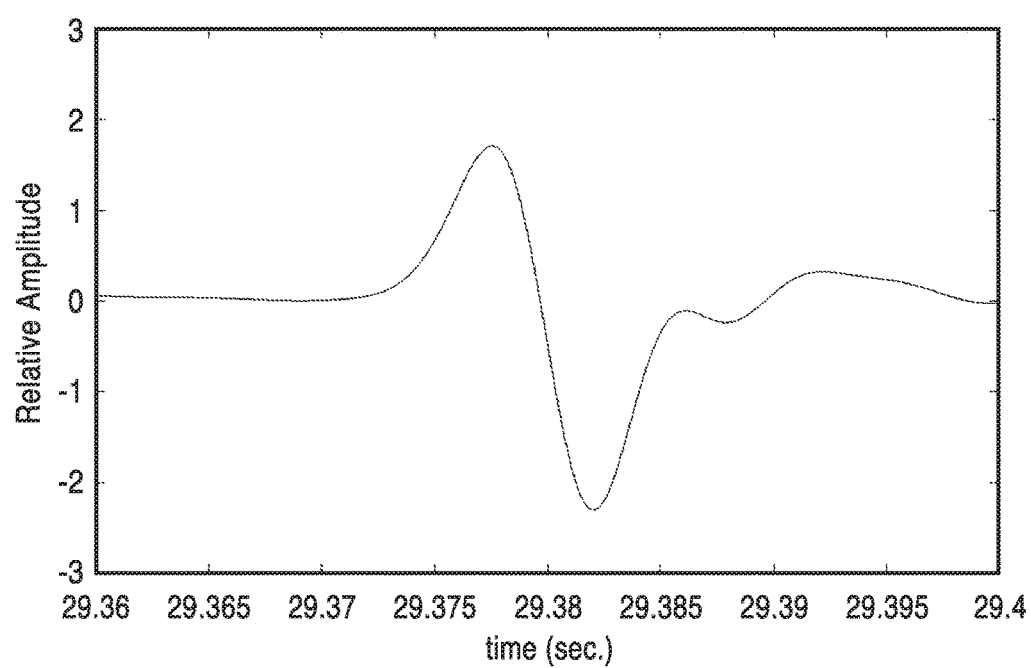

In another configurations, abdominal statistics signal processing application programming 32 may apply abdominal statistics signal processing methods that classify one or more of the following motility events as follows:
 (a) Routines that operate without reliance on signal amplitude and depend only on the time and frequency domain characteristics of motility events.
 (b) Routines that detect the time series profile of motility events exploiting bipolar signal characteristics.
 (c) Routines that detect the time series profile of the specific motility waveform as shown in FIG. 11 through FIG. 13. These plots depict abdominal acoustic motility event signals for a healthy subject obtained from abdominal statistics sensor systems. A 60 second time span record is shown in FIG. 11. FIG. 12 and FIG. 13 display the motility event appearing near the time of 30 seconds. Note the signal lifetime of approximately 10 milliseconds.

Abdominal statistics signal processing routines in accordance with the present description may also classify motility events and reject noise induced signals or physiological phenomena other than motility events.

Figure 14:
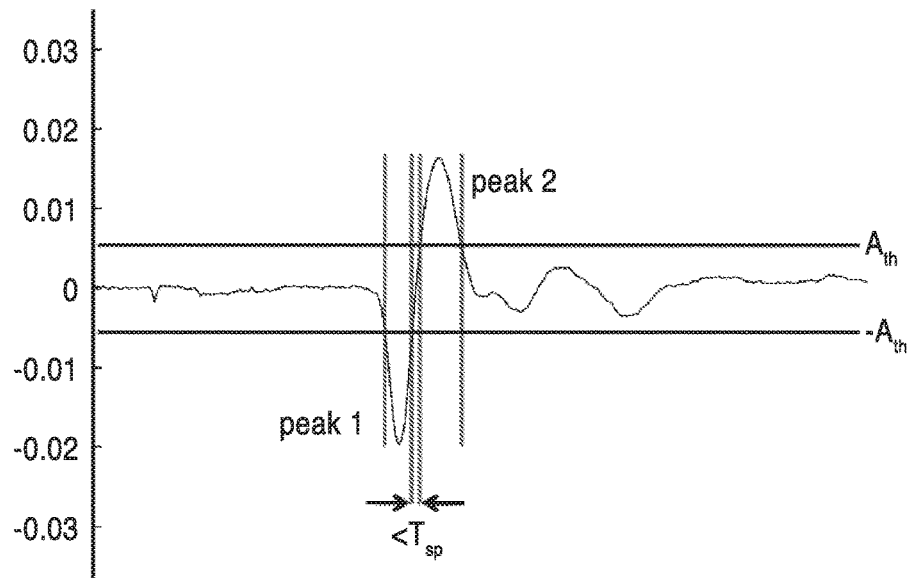
FIG. 14 and FIG. 15 are plots displaying detailed waveform features used in selection and discrimination of events.
Figure 15:
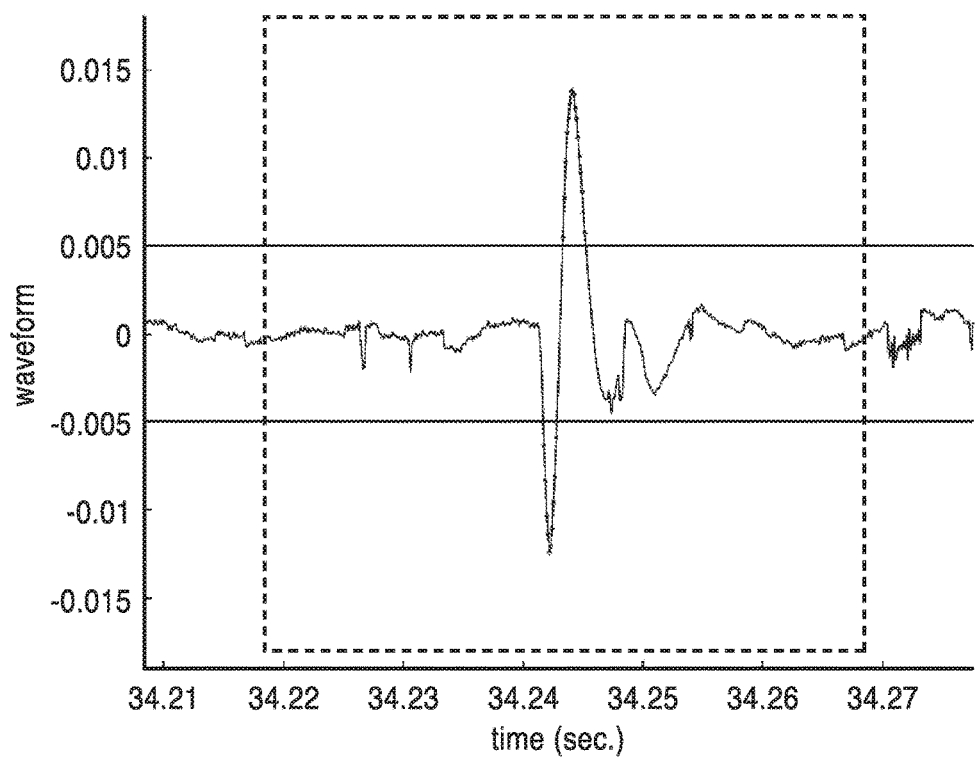

FIG. 14 and FIG. 15 display detailed waveform features used in selection and discrimination of events, with abdominal acoustic motility event signals for a healthy subject obtained from abdominal statistics sensor systems. The waveform of FIG. 14 indicates waveform features applied in discrimination and recognition of motility events. Identified features are sampled accordingly as seen in FIG. 15, where data points are seen at the higher absolute values of the waveform, indicating samples satisfying time and amplitude selection criteria.

Figure 16:
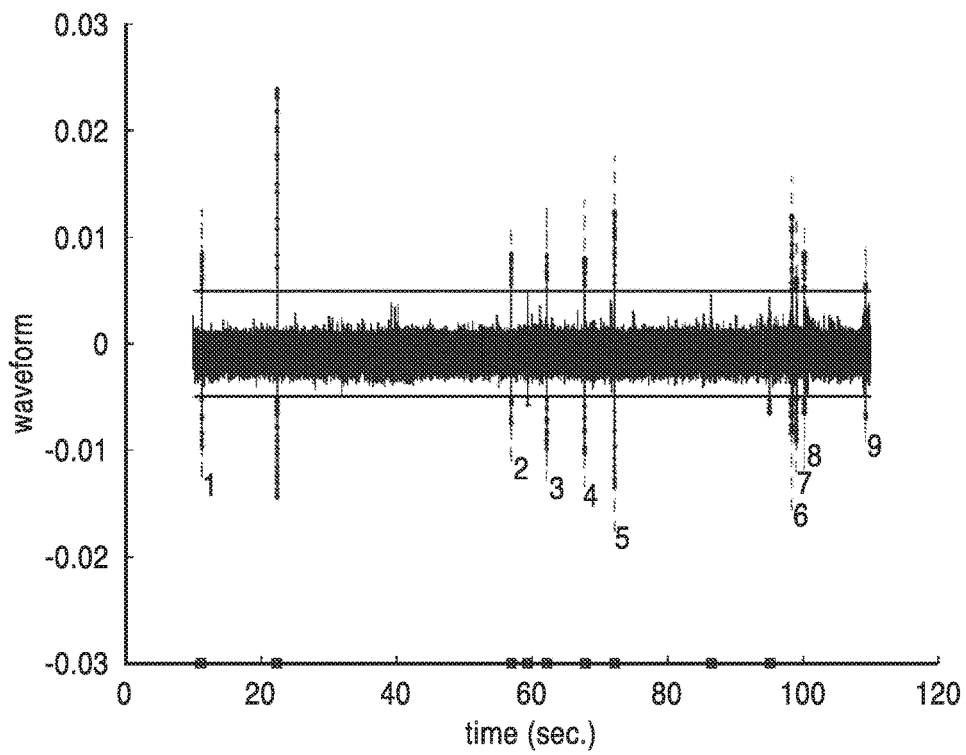
FIG. 16 and FIG. 17 are plots depicting examples of processed data records resulting in selection and discrimination.
Figure 17:
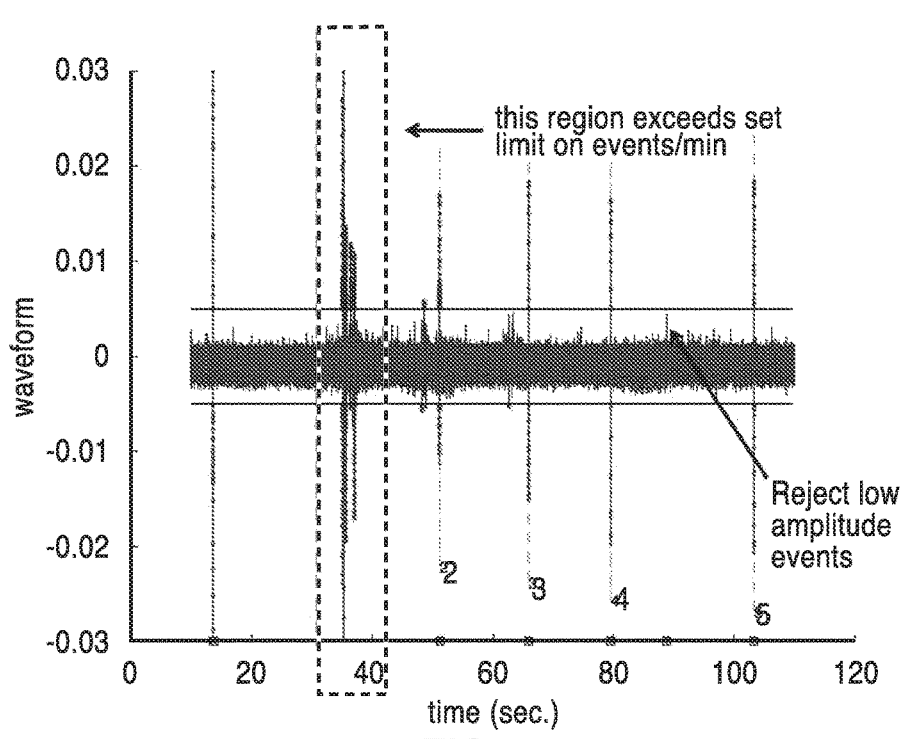

FIG. 16 and FIG. 17 depict examples of processed data records resulting in selection and discrimination, showing abdominal acoustic motility event signals for a healthy subject obtained from abdominal statistics sensor systems. FIG. 16 indicates waveform features that meet criteria for motility events. However, environmental noise or other physiological phenomena not associated with motility must be discriminated against. In FIG. 17, an example illustrates events of incorrect time profile (a number of features appearing at excessive rate in time) and features displaying insufficient amplitude.

Abdominal statistics signal processing programming 32 may also include routines for selection and discrimination based on one or more criteria as described below. The following criteria are based on the investigation of motility events in over 100 subjects, including both healthy state subjects and those afflicted with post operative ileus, gastroparesis, and other disorders:
 (i) Signal Power Time Window Width associated with sampling of the waveform in computation of signal power. Signal power is applied in discrimination where signal power exceeding a threshold indicates presence of noise. Regions of time displaying excessive noise signal power are removed from consideration. Total observation time estimate is adjusted according to time periods removed from consideration due to noise.
 (ii) Signal Power Time Window Stagger is defined and determines overlap between sampling windows. This overlap is adjusted to optimize the capture of noise events while ensuring high computational throughput.
 (iii) Signal High Power Threshold is the value that indicates presence of noise.
 (iv) Consecutive High Power Limit determines in the time domain if an excessive number of windows exceeding threshold have appeared. If this condition is observed, the record period is indicated to be noise.
 (v) Number of Precursor Windows is a parameter that determines the number of windows to be declared as noise and removed from consideration at a time prior to a window for an instance where noise is detected in the window.
 (vi) Number of Precursor Windows is a parameter that determines the number of windows to be declared as noise and removed from consideration at a time after a window for an instance where noise is detected in the window.
 (vii) Amplitude Threshold is the signal amplitude that designates a candidate signal.
 (viii) Peak Detection is a method that detects a time domain feature that rises above amplitude threshold and returns to a level below amplitude threshold.
 (ix) Minimum Peak Width is the width in time associated with a single time domain feature. Time domain peak features having width less than this value are declared as noise events.
 (x) Maximum Peak Width is the width in time associated with a single time domain feature. Time domain peak features having width greater than this value are declared as noise events.
 (xi) Maximum Peak Separation is the maximum time observed between consecutive peaks that separate these from other features. If the separation exceed this threshold, than the two signal peaks are in different groups.

(xii) Minimum Number of Peaks is the minimum number of peaks allowed to for an signal feature to be considered as a motility event.

(xiii) Maximum Number of Peaks is the maximum number of peaks allowed to for an signal feature to be considered as a motility event.

(xiv) Minimum Time Between Groups is the minimum time between consecutive peaks that are to be classified into different groups. This is used to group the peaks together that are then evaluated according to the above rules that describe the motility event.

Abdominal statistics signal processing software 32 may also enable the following applications:

(a) Signal processing methods specifically optimized for detection of migrating motor complex (MMC) events.

(b) Methods that exploit multiple abdominal statistics sensors and apply sensor fusion algorithms for digestive state classification.

(c) Signal processing methods specifically optimized for detection of bowel obstructions.

(d) Signal processing methods specifically optimized for detection of motility abnormalities in functional GI disorders, such as Irritable Bowel Syndrome (IBS).

(e) Signal processing methods specifically optimized for detection of motility abnormalities in Inflammatory Bowel Diseases.

(f) Signal processing methods to optimize feeding in obese subjects.

(g) Signal processing methods specifically optimized for detection and characterization of colic in pediatric subjects.

(h) Signal processing methods specifically optimized for detection of motility abnormalities in neonates with ileus, bowel obstruction, or necrotizing enterocolitis (i) Signal processing methods specifically optimized for detection of ileus in subjects afflicted with pancreatitis.

Software 32 may included abdominal statistics signal processing and sensor deployment routines to enable applications including the following:

(a) Measurement of transit time across the esophageal body to localize motility and estimate transit time across areas of interest (esophagus, stomach, small bowel, colon).

(b) Detection of chewing.

(c) Detection of swallowing.

(d) Classification of food types.

(e) Estimation of gastric emptying time by detection of pyloric emptying.

It should be appreciated that the abdominal statistics system can be configured for performing the above, and other applications as described herein, in various combination, without departing from the teachings of the present disclosure.

Abdominal statistics signal processing software 32 may also be configured for diagnostics or optimal guidance of nutrition type and schedule via application of measurement of motility signals, MMC signals, and other abdominal acoustic signals along with meal ingestion, including the following:

(a) Abdominal statistics monitoring before, during and after a period of meal ingestion type, quantity, and schedule may be varied to enable development of a diagnostic model for an individual subject.

(b) Abdominal statistics products including a meal kit or range of meal kits providing meal materials and other accessories to promote and provide assurance of subject eating according to protocols.

(c) Abdominal statistics products including other stimulants including, for example, chewing gum, pharmaceuticals, and others as well as specific actions that may include exercise, that induce motility actions to assist in the development of operational models for a specific subject digestive processes.

Abdominal statistics signal processing software 32 may also include imaging methods exploiting multi-sensor methods that detect and track the location of a motility event within the intestinal tract.

The abdominal statistics sensor systems 10 may also communicate with ingestible modules that may or may not include acoustic communication and enable tracking of food transit, and include acoustic emitter devices to enable communication between sensors for both usage assurance and calibration of tissue and organ path loss.

Figure 18:
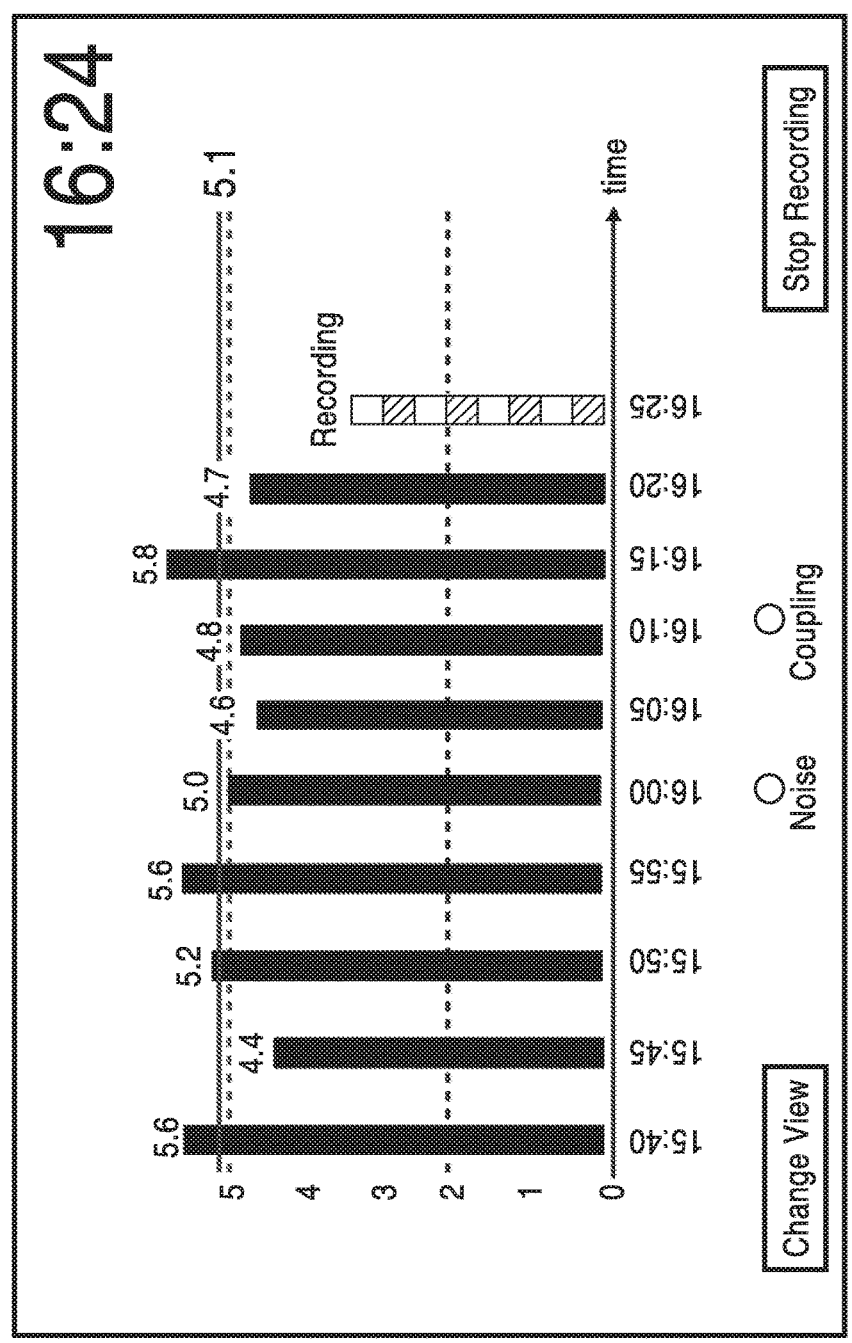
FIG. 18 is a screen output showing an embodiment the abdominal statistics gateway display system.

Abdominal statistics signal software 32 may also include an abdominal statistics gateway display module (e.g. display module 82 shown in FIG. 4B) to provide user guidance and display subject trends. FIG. 18 shows an exemplary abdominal statistics gateway display screen, which may be selected to enable a series of features shown in the figure. Subject motility rate trend view selection with a 5 minute average option is shown. In this example of a touch-panel display, one sees the elapsed time in the upper right, with recent events shown as the bars with their amplitude. Thresholds are seen in the chart as well. In at least one embodiment, these thresholds may be adjusted in response to selecting and sliding the threshold from the touch screen. In a preferred embodiment, the touch screen allows the user to slide to any portion of the collected data, to compress or expand the display of the data, and to provide other related functions.

The abdominal statistics gateway display module 82 shown in FIG. 4B may include features and methods that enable rapid patient assessment and ease of use. These features may include one or more of the following:

(i) Data display based on the familiar bar chart format with labeled motility rate indicator bars.

(ii) Indicators for time averaged motility rate.

(iii) Indicators for time averaged rate corresponding to ileus, healthy state, and intermediate state conditions.

(iv) User selection for change in displayed time period.

(v) Indicators of excessive noise.

(vi) Indicators of error condition due to insufficient sensor coupling or removal of sensors.

(vii) User selection for starting recording, stopping recording, and start of new recording.

(viii) Abdominal statistics control system for data acquisition and display by the state diagram as indicated in FIG. 14.

Additional human subject abdominal statistics applications are also contemplated.

Optimization of nutrition may include the following: (i) Subject food survey for detection of lactose intolerance; (ii) Subject food survey for detection of gluten intolerance; (iii) Subject food survey for detection of other food intolerance; and (iv) Subject food ingestion periods to optimize: (iv)(1) Weight management, (iv)(2) Comfort, (iv)(3) Mental state, (iv)(4) Sleep quality, and (v)(5) Athletic performance.

Optimization of nutrition through introduction of a meal or series of meals selected to promote specific digestive processes along with abdominal statistics monitoring of these processes before, during, and after meals to enable the following capabilities that include but are not limited to (i) subject food survey for detection of lactose intolerance; (ii) subject food survey for detection of gluten intolerance; (iii)

subject food survey for detection of other food intolerance; and (iv) subject food ingestion periods to optimize one or more of: weight management, comfort, mental state, sleep quality, athletic performance, and development of models for subject response to ingestion that enables optimization of nutrition or diagnostic capability for disease detection.

Methods that enable measurement of transit time may include: (i) measurement of esophageal transit time, (ii) measurement of stomach food residency and transit time, (iii) measurement of stomach emptying for diagnosis of gastroparesis condition, and (iv) measurement of intestinal tract transit times.

Methods that enable classification of food type and composition may include (i) determination of food type through detection of acoustic signatures associated with chewing and swallowing; (ii) determination of food type through detection of acoustic signatures associated with stomach digestive processed, and (iii) determination of food type through detection of acoustic signatures associated with intestinal digestive processes.

The systems and methods of the present description may also include veterinary subject product comprising multi-sensor, robust systems integrated with animal harnesses and wearable systems. Veterinary subject product applications may comprise nutrition optimization routines, including: livestock production optimization, feed operations optimization and scheduling, early detection of digestive disorders, including colic, a dynamic ileus, mechanical bowel obstructions, volvulus, and other common conditions in small and large animals, optimization of nutrition for individual animals and animal cohorts.

Furthermore, any of the application software routines detailed above for human monitoring may be configured for application with animal subjects for optimization of animal health and livestock production.

The abdominal statistics system 10 described herein may be readily implemented to include one or more computer processor devices (e.g., CPU, microprocessor, microcontroller, computer enabled ASIC, etc.) and associated memory (e.g., RAM, DRAM, NVRAM, FLASH, computer readable media, etc.) whereby programming stored in the memory and executable on the processor perform the steps of the various process methods described herein. The computer and memory devices were not depicted in the diagrams for the sake of simplicity of illustration, as one of ordinary skill in the art recognizes the use of computer devices for carrying out steps involved with signal generation and processing. The presented technology is non-limiting with regard to memory and computer-readable media, insofar as these are non-transitory, and thus not constituting a transitory electronic signal.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. An apparatus for assessing one or more patient digestive processes, the apparatus comprising: (a) one or more digestive acoustic sensor modules configured to be coupled to a patient's abdomen; (b) an acoustic sensor disposed within each said sensor module, said acoustic sensor configured for registering sounds associated with digestive processes of the patient; (c) a vibration actuator disposed within each said sensor module, said vibration actuator configured for communicating a vibratory signal to the one or more sensor modules; (d) a computer processor; and (e) a non-transitory computer-readable memory storing instructions executable by the computer processor; (f) wherein said instructions, when executed by the computer processor, perform steps comprising: (i) registering digestive motility events received from said acoustic sensor when an acoustic signal from said acoustic sensors matches one or more predetermined digestive motility acoustic patterns; and (ii) classifying one or more motility events based on said registered digestive motility events while rejecting noise induced signals or physiological phenomena other than motility events.

2. The apparatus of any preceding embodiment, wherein said digestive events comprise sounds emanating in the gastrointestinal tract of the patient.

3. The apparatus of any preceding embodiment, wherein said digestive events comprise sounds emanating from the mouth, or along the esophagus of the patient, or a combination thereof.

4. The apparatus of any preceding embodiment, further comprising: a removable data storage module for storing data relating to said digestive motility events; wherein the digestive motility event data is configured for display on an external electronic device.

5. The apparatus of any preceding embodiment, wherein said instructions, when executed by the computer processor, perform steps comprising: validating a registered digestive motility event as a function of an acoustic signal from said acoustic sensors exceeding a selected amplitude threshold.

6. The apparatus of any preceding embodiment, further comprising: a user interface module; wherein said instructions are further configured for receiving user commands through said user interface for controlling assessment of patient digestive processes.

7. The apparatus of any preceding embodiment, wherein said instructions, when executed by the computer processor, perform steps comprising: determining proper positioning of the one or more sensor modules on the patient by activating said vibration actuator in at least one of said sensor modules; and registering acoustic signals generated by said vibration actuator on a second of said sensors.

8. The apparatus of any preceding embodiment, wherein said instructions, when executed by the computer processor, perform steps comprising: calibrating acoustic coupling levels of said one or more sensor modules in response to amplitude levels of the registered acoustics signals from said vibration actuator.

9. The apparatus of any preceding embodiment: wherein the one or more sensor modules comprises a pair of sensor modules; and wherein said instructions, when executed by the computer processor, perform steps comprising determining spacing between said pair of sensor modules in response to registering a time delay between actuating said vibration actuator and registered acoustics from said vibration actuator.

10. The apparatus of any preceding embodiment: wherein the processor is housed in a controller module remotely coupled to the one or more sensor modules; the processor module comprising a display; wherein the display is configured for displaying statistics relating to said digestive motility events.

11. The apparatus of any preceding embodiment: wherein said sensor module comprises a housing configured to retain said vibration actuator and acoustic sensor; said housing comprising an annular flange configured for epidermal retention on the patient by attachment via an adhesive bandage.

12. An apparatus for monitoring one or more patient digestive processes via an acoustic sensor configured for registering sounds associated with digestive processes, the apparatus comprising: (a) a computer processor configured to be coupled to the acoustic sensor; and (b) a non-transitory computer-readable memory storing instructions executable by the computer processor; (c) wherein said instructions, when executed by the computer processor, perform steps comprising: (i) registering digestive motility events received from said acoustic sensor when an acoustic signal from said acoustic sensors matches one or more predetermined digestive motility acoustic patterns; and (ii) classifying one or more motility events based on said registered digestive motility events while rejecting noise induced signals or physiological phenomena other than motility events.

13. The apparatus of any preceding embodiment, wherein said digestive events comprise sounds emanating in the gastrointestinal tract of the patient.

14. The apparatus of any preceding embodiment, wherein said digestive events comprise sounds emanating from the mouth, or along the esophagus of the patient, or a combination thereof.

15. The apparatus of any preceding embodiment, further comprising: a removable data storage module for storing data relating to said digestive motility events; wherein the digestive motility event data is configured for display on an external electronic device.

16. The apparatus of any preceding embodiment, wherein said instructions are further configured for: validating a registered digestive motility event as a function of an acoustic signal from said acoustic sensors exceeding a selected amplitude threshold.

17. The apparatus of any preceding embodiment, further comprising: a user interface module; wherein said instructions are further configured for receiving user commands through said user interface module for controlling assessment of patient digestive processes.

18. The apparatus of any preceding embodiment, further comprising: a vibration actuator coupled to the processor; the vibration actuator configured for communicating a vibratory signal to the acoustic sensor; wherein said instructions, when executed by the computer processor, perform steps comprising: (i) determining proper positioning of the acoustic sensor on the patient by activating said vibration actuator; and (ii) registering acoustic signals generated by said vibration actuator on said acoustic sensor.

19. The apparatus of any preceding embodiment, wherein said instructions, when executed by the computer processor, perform steps comprising: calibrating acoustic coupling levels of said acoustic sensor in response to amplitude levels of the registered acoustics signals from said vibration actuator.

20. The apparatus of any preceding embodiment, further comprising: a pair of acoustic sensors; wherein said instructions, when executed by the computer processor, perform steps comprising determining spacing between said pair acoustic sensors in response to registering a time delay between actuating said vibration actuator and registered acoustics from said vibration actuator.

21. The apparatus of any preceding embodiment: wherein the processor is housed in a controller module remotely coupled to the one or more sensor modules; the processor module comprising a display; wherein the display is configured for displaying statistics relating to said digestive motility events.

22. A method for monitoring one or more patient digestive processes via an acoustic sensor configured for registering sounds associated with digestive processes, the method comprising: receiving user commands for controlling assessment of patient digestive processes; determining proper positioning of the acoustic sensor on the patient in response to activating a vibration actuator and registering acoustic signals generated by said vibration actuator on the acoustic sensors; calibrating acoustic coupling levels of said acoustic sensor in response to amplitude levels of registered acoustics from said vibration actuator; registering digestive motility events received from said acoustic sensor when an acoustic signal from said acoustic sensor matches one or more predetermined digestive motility acoustic patterns; classifying one or more motility events based on said registered digestive motility events while rejecting noise induced signals or physiological phenomena other than motility events; and displaying statistics on said digestive motility events.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for assessing one or more patient digestive processes, the apparatus comprising:
   (a) one or more digestive acoustic sensor modules configured to be coupled to a patient's abdomen;
   (b) an acoustic sensor disposed within each said sensor module, said acoustic sensor configured for registering sounds associated with digestive processes of the patient;
   (c) a vibration actuator disposed within each said sensor module, said vibration actuator configured for communicating a vibratory signal to the one or more sensor modules;
   (d) a computer processor; and
   (e) a non-transitory computer-readable memory storing instructions executable by the computer processor;
   (f) wherein said instructions, when executed by the computer processor, perform steps comprising:
      (i) registering digestive motility events received from said acoustic sensor when an acoustic signal from said acoustic sensor matches one or more predetermined digestive motility acoustic patterns;
      (ii) classifying one or more motility events based on said registered digestive motility events while rejecting noise induced signals or physiological phenomena other than motility events;
      (iii) determining proper positioning of the one or more sensor modules on the patient by activating said vibration actuator in at least one of said sensor modules; and
      (iv) registering acoustic signals generated by said vibration actuator on a second of said sensor modules.

2. The apparatus of claim 1, wherein said digestive events comprise sounds emanating in the gastrointestinal tract of the patient.

3. The apparatus of claim 1, wherein said digestive events comprise sounds emanating from the mouth, or along the esophagus of the patient, or a combination thereof.

4. The apparatus of claim 1, further comprising:
   a removable data storage module for storing data relating to said digestive motility events;
   wherein the digestive motility event data is configured for display on an external electronic device.

5. The apparatus of claim 1, wherein said instructions, when executed by the computer processor, perform steps comprising:
   validating a registered digestive motility event as a function of an acoustic signal from said acoustic sensors exceeding a selected amplitude threshold.

6. The apparatus of claim 1, further comprising:
   a user interface module;
   wherein said instructions are further configured for receiving user commands through said user interface for controlling assessment of patient digestive processes.

7. The apparatus of claim 1, wherein said instructions, when executed by the computer processor, perform steps comprising:
   calibrating acoustic coupling levels of said one or more sensor modules in response to amplitude levels of the registered acoustics signals from said vibration actuator.

8. The apparatus of claim 7:
   wherein the one or more sensor modules comprises a pair of sensor modules; and
   wherein said instructions, when executed by the computer processor, perform steps comprising determining spacing between said pair of sensor modules in response to registering a time delay between actuating said vibration actuator and registered acoustics from said vibration actuator.

9. The apparatus of claim 1:
   wherein the processor is housed in a controller module remotely coupled to the one or more sensor modules;
   the processor module comprising a display;
   wherein the display is configured for displaying statistics relating to said digestive motility events.

10. The apparatus of claim 1:
    wherein said sensor module comprises a housing configured to retain said vibration actuator and acoustic sensor;
    said housing comprising an annular flange configured for epidermal retention on the patient by attachment via an adhesive bandage.

11. An apparatus for monitoring one or more patient digestive processes via an acoustic sensor configured for registering sounds associated with digestive processes, the apparatus comprising:

(a) a computer processor configured to be coupled to the acoustic sensor; and
(b) a non-transitory computer-readable memory storing instructions executable by the computer processor;
(c) a vibration actuator coupled to the processor, the vibration actuator configured for communicating a vibratory signal to the acoustic sensor;
(d) wherein said instructions, when executed by the computer processor, perform steps comprising:
  (i) registering digestive motility events received from said acoustic sensor when an acoustic signal from said acoustic sensor matches one or more predetermined digestive motility acoustic patterns;
  (ii) classifying one or more motility events based on said registered digestive motility events while rejecting noise induced signals or physiological phenomena other than motility events;
  (iii) determining proper positioning of the acoustic sensor on the patient by activating said vibration actuator; and
  (iv) registering acoustic signals generated by said vibration actuator on said acoustic sensor.

12. The apparatus of claim 11, wherein said digestive events comprise sounds emanating in the gastrointestinal tract of the patient.

13. The apparatus of claim 11, wherein said digestive events comprise sounds emanating from the mouth, or along the esophagus of the patient, or a combination thereof.

14. The apparatus of claim 11, further comprising:
a removable data storage module for storing data relating to said digestive motility events;
wherein the digestive motility event data is configured for display on an external electronic device.

15. The apparatus of claim 11, wherein said instructions are further configured for:
validating a registered digestive motility event as a function of an acoustic signal from said acoustic sensors exceeding a selected amplitude threshold.

16. The apparatus of claim 11, further comprising:
a user interface module;
wherein said instructions are further configured for receiving user commands through said user interface module for controlling assessment of patient digestive processes.

17. The apparatus of claim 11, wherein said instructions, when executed by the computer processor, perform steps comprising:
calibrating acoustic coupling levels of said acoustic sensor in response to amplitude levels of the registered acoustics signals from said vibration actuator.

18. The apparatus of claim 17, further comprising:
a pair of acoustic sensors;
wherein said instructions, when executed by the computer processor, perform steps comprising determining spacing between said pair acoustic sensors in response to registering a time delay between actuating said vibration actuator and registered acoustics from said vibration actuator.

19. The apparatus of claim 11:
wherein the processor is housed in a controller module remotely coupled to the one or more sensor modules;
the processor module comprising a display;
wherein the display is configured for displaying statistics relating to said digestive motility events.

20. A method for monitoring one or more patient digestive processes via an acoustic sensor configured for registering sounds associated with digestive processes, the method comprising:
receiving user commands for controlling assessment of patient digestive processes;
determining proper positioning of the acoustic sensor on the patient in response to activating a vibration actuator and registering acoustic signals generated by said vibration actuator on the acoustic sensors;
calibrating acoustic coupling levels of said acoustic sensor in response to amplitude levels of registered acoustics from said vibration actuator;
registering digestive motility events received from said acoustic sensor when an acoustic signal from said acoustic sensor matches one or more predetermined digestive motility acoustic patterns;
classifying one or more motility events based on said registered digestive motility events while rejecting noise induced signals or physiological phenomena other than motility events; and
displaying statistics on said digestive motility events.

* * * * *